United States Patent
Shi et al.

(10) Patent No.: US 11,826,145 B2
(45) Date of Patent: Nov. 28, 2023

(54) TAIL PRESSING TYPE DISPOSABLE SAFETY LANCET

(71) Applicant: STERILANCE MEDICAL (SUZHOU) INC., Jiangsu (CN)

(72) Inventors: Guoping Shi, Suzhou (CN); Anthony Scott Horstman, Suzhou (CN)

(73) Assignee: STERILANCE MEDICAL (SUZHOU) INC., Suzhou (CN)

( * ) Notice: Subject to any disclaimer, the term of this patent is extended or adjusted under 35 U.S.C. 154(b) by 728 days.

(21) Appl. No.: 16/975,174

(22) PCT Filed: Feb. 22, 2019

(86) PCT No.: PCT/CN2019/075913
§ 371 (c)(1),
(2) Date: Aug. 24, 2020

(87) PCT Pub. No.: WO2019/161787
PCT Pub. Date: Aug. 29, 2019

(65) Prior Publication Data
US 2021/0113125 A1    Apr. 22, 2021

(30) Foreign Application Priority Data
Feb. 24, 2018    (CN) .......................... 201810157218.6

(51) Int. Cl.
*A61B 5/151*    (2006.01)
*A61B 5/15*    (2006.01)

(52) U.S. Cl.
CPC ...... *A61B 5/150022* (2013.01); *A61B 5/1513* (2013.01); *A61B 5/15019* (2013.01);
(Continued)

(58) Field of Classification Search
None
See application file for complete search history.

(56) References Cited

U.S. PATENT DOCUMENTS

| 6,432,120 B1* | 8/2002 | Teo ................. A61B 5/150503 |
| | | 606/181 |
| 2008/0039886 A1* | 2/2008 | Shi .................. A61B 5/150519 |
| | | 606/182 |

(Continued)

FOREIGN PATENT DOCUMENTS

| CN | 107157494 A | 9/2017 |
| CN | 108186029 A | 6/2018 |
| EP | 3 708 081 A1 | 9/2020 |

OTHER PUBLICATIONS

Apr. 19, 2019 Search Report issued in International Patent Application No. PCT/CN2019/075913.

*Primary Examiner* — Etsub D Berhanu
*Assistant Examiner* — Martin Nathan Ortega
(74) *Attorney, Agent, or Firm* — Oliff PLC

(57) ABSTRACT

A tail pressing type disposable safety lancet includes a shell, a lancet core, a spring and tail cover. The shell has an elastic arm for locking the lancet core, wherein: the tail cover has an active locking part for locking and the elastic arm has a passive locking part for locking correspondingly; the positions, the fitting time of the active locking part and the passive locking part correlate with the active and passive unlocking parts; when the tail cover is pressed during use, it forces the lancet core to unlock for ejection and puncturing, and the tail cover and elastic arm enter the locking state and cannot be used again. After use of the safety lancet, the tail cover permanently locks on the elastic arm of the shell, ensuring the safety of single use, and the user visually recognizes the tail cover is retracted at the tail of the shell.

9 Claims, 14 Drawing Sheets

(52) U.S. Cl.
CPC ...... *A61B 5/15113* (2013.01); *A61B 5/15117* (2013.01); *A61B 5/15144* (2013.01); *A61B 5/150412* (2013.01); *A61B 5/150549* (2013.01); *A61B 5/150893* (2013.01); *A61B 2560/04* (2013.01)

(56) References Cited

U.S. PATENT DOCUMENTS

| | | | |
|---|---|---|---|
| 2009/0069832 A1* | 3/2009 | Kitamura | A61B 5/150824 606/181 |
| 2011/0066077 A1* | 3/2011 | Chang | A61B 5/150022 600/576 |
| 2012/0215246 A1* | 8/2012 | Hyoue | A61B 5/15019 606/182 |

* cited by examiner ns with the continuous improvement of technology and the improvement of people's living standards, the concept of such product design is: On the premise of ensuring the effect of blood sampling, more attention is paid to use safety and user experience. Therefore, the subject of the present invention is how to solve the above problem in an effective way.

TAIL PRESSING TYPE DISPOSABLE SAFETY LANCET

TECHNICAL FIELD

The present invention relates to the medical lancing device field, especially a tail pressing type disposable safety lancet. The safety lancet has its own ejection mechanism, which not only has an obvious marking after use, but also cannot be used again, thus ensuring the safety of single use of the safety lancet.

BACKGROUND OF INVENTION

In the field of safety lancet, the disposable lancet is popular among medical personnel and patients because of its small size, safety use and convenient operation. It is currently widely used by various medical institutions and diabetics. The safety lancet has a built-in ejection mechanism and compact structure, and it's disposable as a whole to be safe and convenient, so it has very strong market development potential.

Chinese patent CN107007289A discloses an invention patent application titled "Pressing Type Disposable Safety Lancet with Spring Pilot Structure". Although the innovation of the patent is that the spring pilot structure and the unlocking mechanism are skillfully associated to skillfully use one structure for two functions, thereby achieving the dual effect of piloting and unlocking, the patented solution presents a representative basic structure of a tail pressing type safety lancet, which is mainly composed of a shell, a lancet core, a spring and a tail cover. In the assembled state, the lancet core is positioned and locked on the elastic arm in the shell, and the lancet core and the shell are slidably connected by a sliding channel in the ejection direction of the needle tip; the front end of the spring acts on the lancet core and the rear end acts on the tail cover; the tail cover is installed at the end of the shell and is slidably connected with the shell in the ejection direction of the needle tip. When the head of the safety lancet is aligned with the blood sampling site, the tail cover is pressed, and the bevel on the tail cover forces the elastic arm to open, triggering the unhooking of the lancet core and the ejection and puncturing under the push of the spring.

Despite the mature basic structure, reliable ejection mechanism, and distinctive structural features of the above-mentioned tail pressing type safety lancet, there are still some shortcomings from the perspective of safety in use: First, as the tail cover completely rebounds after being pressed, its forms before and after use cannot be directly identified from the appearance; Second, even after the safety lancet is used, if a needle is pushed back from the front needle outlet hole, the lancet core can be loaded and used again.

The design of previous such products focused more on the effect of blood sampling. However, with the continuous improvement of technology and the improvement of people's living standards, the concept of such product design is: On the premise of ensuring the effect of blood sampling, more attention is paid to use safety and user experience. Therefore, the subject of the present invention is how to solve the above problem in an effective way.

DISCLOSURE OF THE INVENTION

In view of the shortcomings of the above prior art, the present invention provides a tail pressing type disposable safety lancet, which aims to solve the safety problem that the tail pressing type safety lancet cannot be reused.

In order to achieve the above purpose, the technical solution adopted by the present invention is: a tail pressing type disposable safety lancet consisting of a shell, a lancet core, a spring and a tail cover.

The shell forms an ejecting cavity, the lancet core is located in the ejecting cavity, the shell is provided with elastic arms extending inward, and the elastic arm is provided with a hook or end face for locking the lancet core, and the lancet core is provided with a clamping face corresponding to the hook or end face; in the ejection ready state, the front end of the spring presses against the lancet core, and the clamping face of the lancet core presses against the hook or end face of the elastic arm, so that the lancet core is positioned and locked in the ejecting cavity of the shell.

The tail cover is installed at the tail of the shell, the tail cover and the shell are slidably connected in the axial direction of the safety lancet, and the tail cover is provided with a limit relative to the rear end of the shell in the sliding direction; in the ejection ready state, the rear end of the spring presses against the tail cover, forcing the tail cover to be in the rear limit position relative to the shell in the sliding direction.

The tail cover is provided with an active unlocking part, and the active unlocking part is provided with an action end and the elastic arm is provided with a passive unlocking part corresponding to the active unlocking part, and the passive unlocking part is provided with an action, and at least one of the action end of the active unlocking part and the action end of the passive unlocking part is an unlocking bevel.

Its innovation lies in: the tail cover is provided with an active locking part, and the active locking part is provided with an action end and the elastic arm is provided with a passive locking part corresponding to the active locking part, and the passive locking part is provided with an action, and one of the action end of the active locking part and the action end of the passive locking part is provided with a locking hook and the other is provided with a locking face.

In the ejection ready state, taking the axial direction of the safety lancet as a reference, the axial projection distance between the action end of active unlocking part and the action end of passive unlocking part is less than or greater than the axial projection distance between the action end of active locking part and the action end of passive locking part; taking the radial direction of the safety lancet as a reference, the distance between the action end of the active locking part and the radial center of the safety lancet is greater than that between the action end of the passive locking part and the radial center of the safety lancet.

In the use state, when the tail cover is pushed, the tail cover moves forward relative to the shell, and the action end of active unlocking part on the tail cover meets the action end of passive unlocking part on the elastic arm, and forces the end of the elastic arm to open laterally under the action of the unlocking bevel, and when the hook or end face of the elastic arm is out of the locking critical point, the lancet core will be triggered to puncture under the action of spring; after the ejection and puncturing, since the end of the elastic arm is in a laterally expanded state, the distance from the action end of passive locking part to the radial center of the safety lancet is close to the distance from the action end of active locking part to the radial center of the safety lancet, and at this moment, the tail cover continues to move forward and the action end of active locking part on the tail cover and the action end of passive locking part on the elastic arm fit with each other through the locking hook and the locking face, forcing the tail cover and elastic arm to enter the locking state and the tail cover is in the retracted state at the tail of the safety lancet.

The above described technical solution and the change are explained as follows:

1. In above described technical solution, the "shell", "lancet core", "spring" and "tail cover" are the basic structures of the tail pressing type disposable lancet, and the basic function and function are the prior art.
2. In above described technical solution, the "front" in the "front end", "front part" and "forward" means the pointing direction of the needle tip in the lancet. The "rear" in said "rear end" means the direction opposite to the "front".
3. In above described technical solution, the "bevel" in the "unlocking bevel" includes the flat face, cambered face or tapered face, but it's always set obliquely in relative to the axis of lancing device to constitute a bevel. In other words, the bevel has four types: the bevel in the form of flat face, the bevel in the form of concave face (the bevel comprises several straight lines in the oblique direction, and the concave face or convex face are formed in the vertical direction, but it's substantially bevel), the bevel in the form of tapered face and the bevel in the form of cambered face (the bevel comprises at least one concave arc or/and convex arc in the oblique direction, but it's substantially bevel). In the present invention, any type is applicable and it could be determined according to the practical situation. Wherein, the first type is the bevel in the form of flat face; the second type is the bevel in the form of concave face; the third type is the bevel in the form of tapered face; and the fourth type is the bevel in the form of cambered face.
4. In above described technical solution, the head of the shell can be added with an adjusting head structure, so that the puncturing depth can be adjusted. This doesn't affect the realization of the purpose of present invention.
5. The tail pressing type safety lancet of present invention consists of two structures of twist cap and cover cap. That is, the disposable lancet is usually designed with the protection cap, and the structure of protection cap could be the twist cap type or cover cap type. This doesn't affect the realization of the purpose of present invention.

The design principles and ideas of the present invention are: In order to ensure that the tail pressing type safety lancet cannot be reused, the present invention adopts the following technical ideas: First, the tail cover is provided with an active locking part for locking and the elastic arm is provided with a passive locking part for locking correspondingly; Secondly, in the safety lancet, the positions of the active locking part and the passive locking part are correlated with the positions of the active unlocking part and the passive unlocking part, that is, the fitting between the active locking part and the passive locking part depends on the fitting between the active unlocking part and the passive unlocking part in the position; Third, in the safety lancet, the fitting time between the active locking part and the passive locking part is correlated with the fitting time between the active unlocking part and the passive unlocking part to produce a prescribed timing relationship, that is, only when the active unlocking part and the passive unlocking part fit earlier, can the active locking part and the passive locking part fit later.

Due to the application of the above described technical solution, the present invention has the following advantages and effect in comparison with the prior art:

1. After the safety lancet of the present invention is used, as the tail cover is permanently locked on the elastic arm of the shell, even if a needle is used to push the lancet core through the needle outlet hole at the front end, the lancet core can't be loaded and used again, therefore, the safety lancet is truly a disposable medical blood sampling product, which theoretically ensures the safety of single use.
2. After the safety lancet of the present invention is used, as the tail cover is permanently locked on the elastic arm of the shell, the tail cover is obviously retracted at the tail of the shell, so that the user can visually identify the different shapes of the safety lancet before and after use. This effect is not only conducive to the safe use of safety lancet, but also improves the user experience.
3. The present invention has reasonable structural design and ingenious technical ideas, which ensures that the tail pressing safety lancet can not be reused, and has outstanding substantive characteristics and remarkable progress compared with the prior art.

The number description of above described drawings is as follows:

1. Shell; 2. Lancet core; 3. Spring; 4. Tail cover; 5. Elastic arm; 6. Hook; 7. Retractile neck; 8. Clamping face; 9. Needle outlet hole; 10. Unlocking bevel; 11. Twist cap; 12. Active unlocking part; 13. Passive unlocking part; 14. Active locking part; 15. Twisting part; 16. Protection rod; 17. Passive locking part; 18. Locking hook; 19. Locking face; 20. Notch; 21. Boss; 22. Elastic leg; 23. Protruding rib; 24. External hook; 25. Gap.

SPECIFIC EMBODIMENT

With reference to the accompanying drawings and embodiment, the present invention will be described in detail.

Embodiment: A Tail Pressing Type Disposable Safety Lancet

Figure 1:
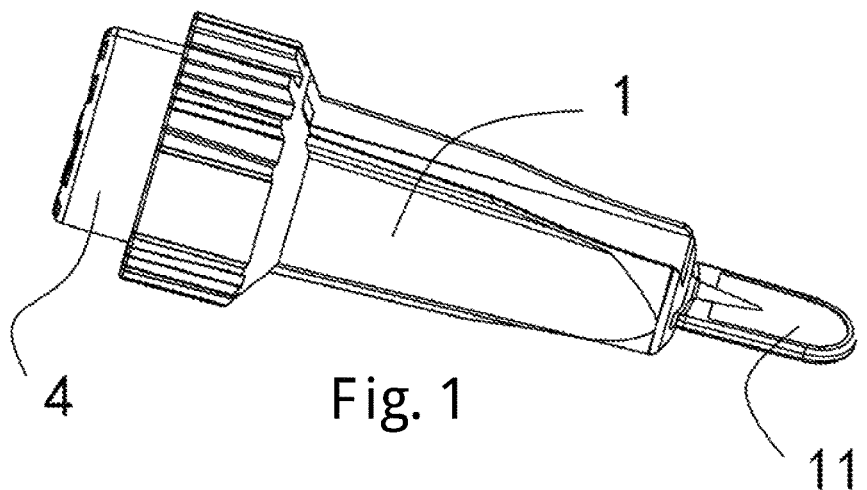
FIG. 1 is the perspective view of safety lancet of an embodiment of present invention.
Figure 2:
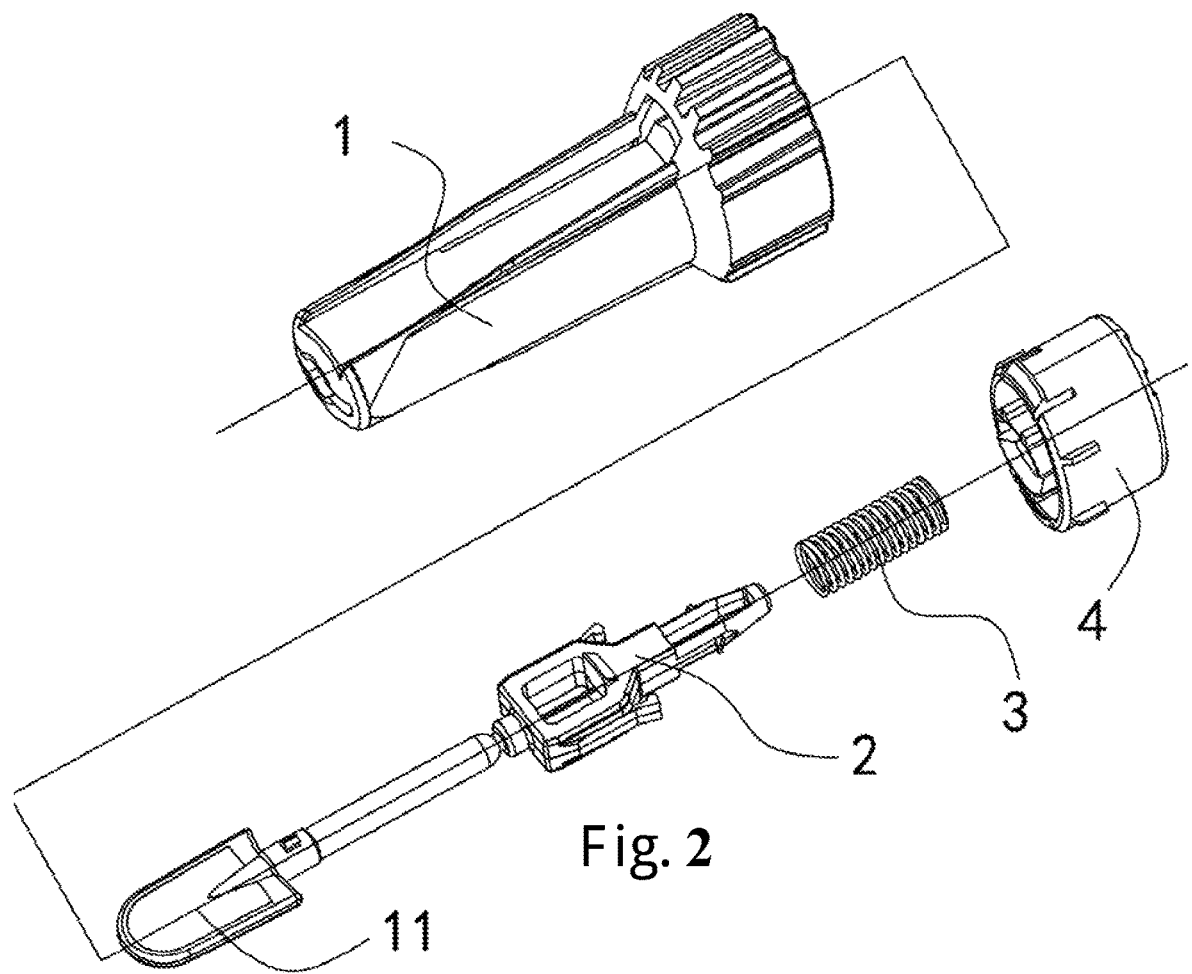
FIG. 2 is the exploded view of safety lancet of an embodiment of present invention.

The safety lancet consists of a shell 1, a lancet core 2, a twist cap 11, a spring 3 and a tail cover 4 (see FIGS. 1 and 2).

Figure 3:
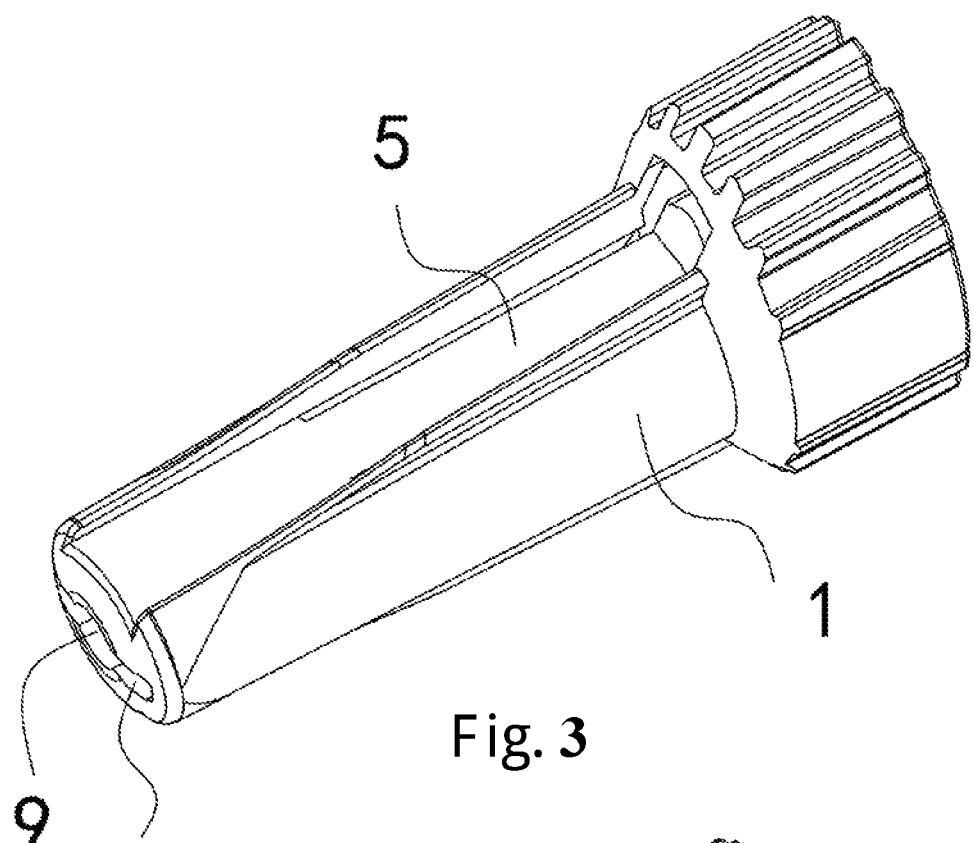
FIG. 3 is the first perspective view of the shell of an embodiment of present invention.
Figure 4:
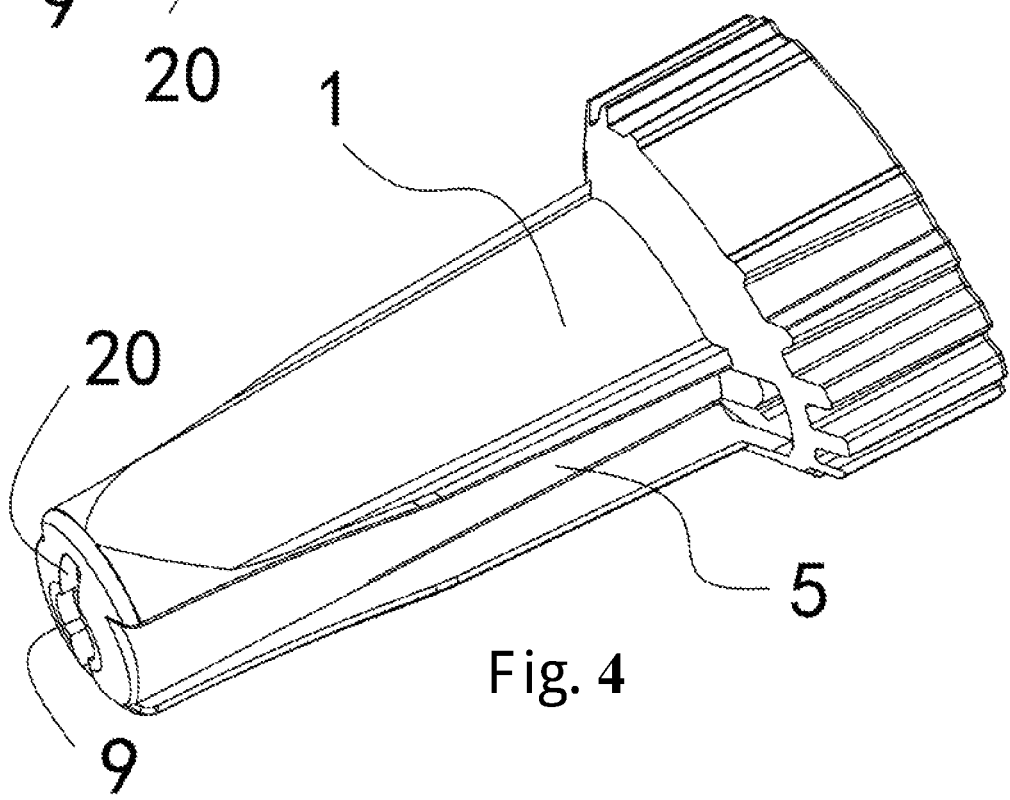
FIG. 4 is the second perspective view of the shell of an embodiment of present invention.
Figure 5:
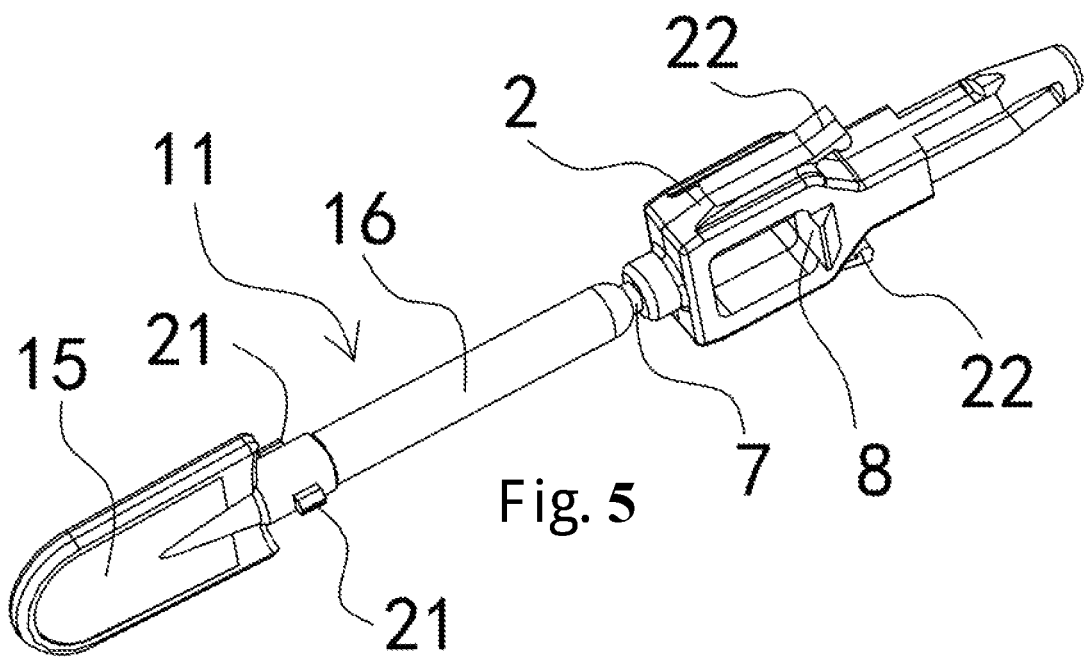
FIG. 5 is the perspective view of the lancet core and twist cap of an embodiment of present invention.
Figure 6:
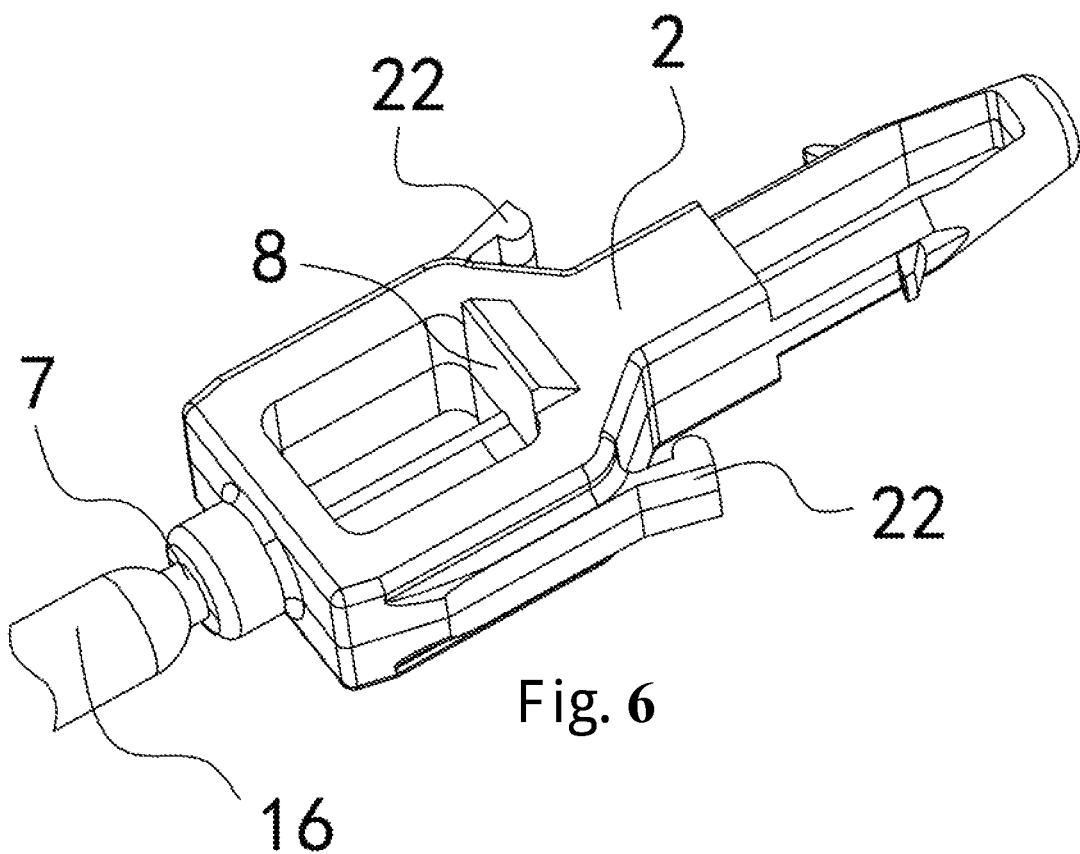
FIG. 6 is the enlarged view of lancet core.
Figure 11:
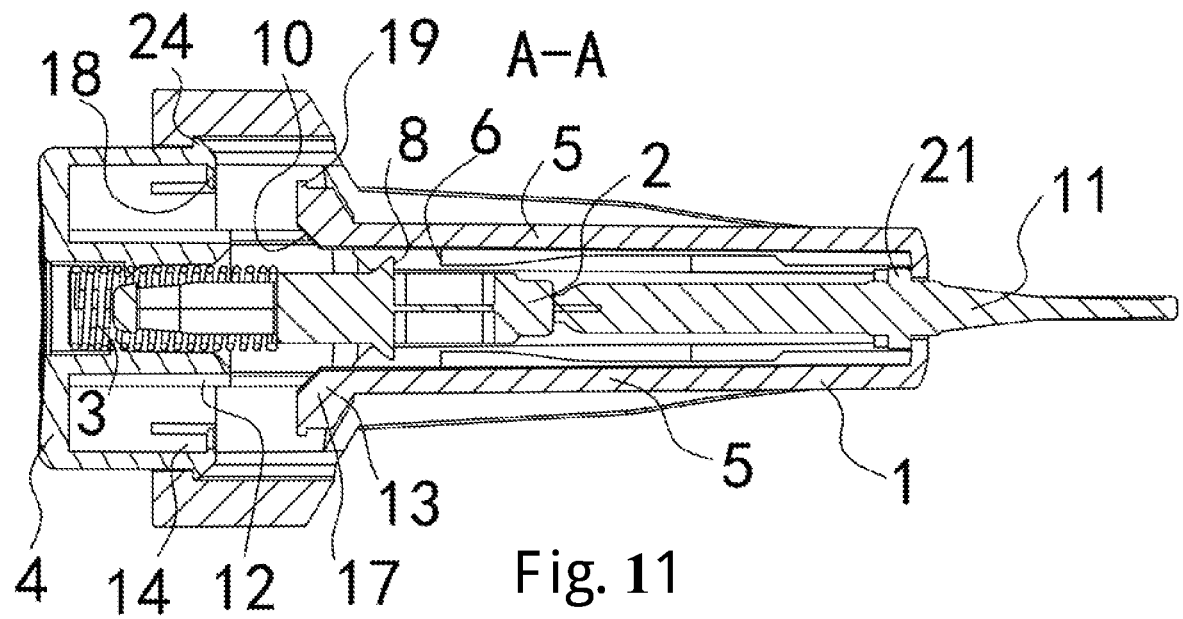
FIG. 11 is the A-A section view of an embodiment of present invention in the initial assembly state.
Figure 12:
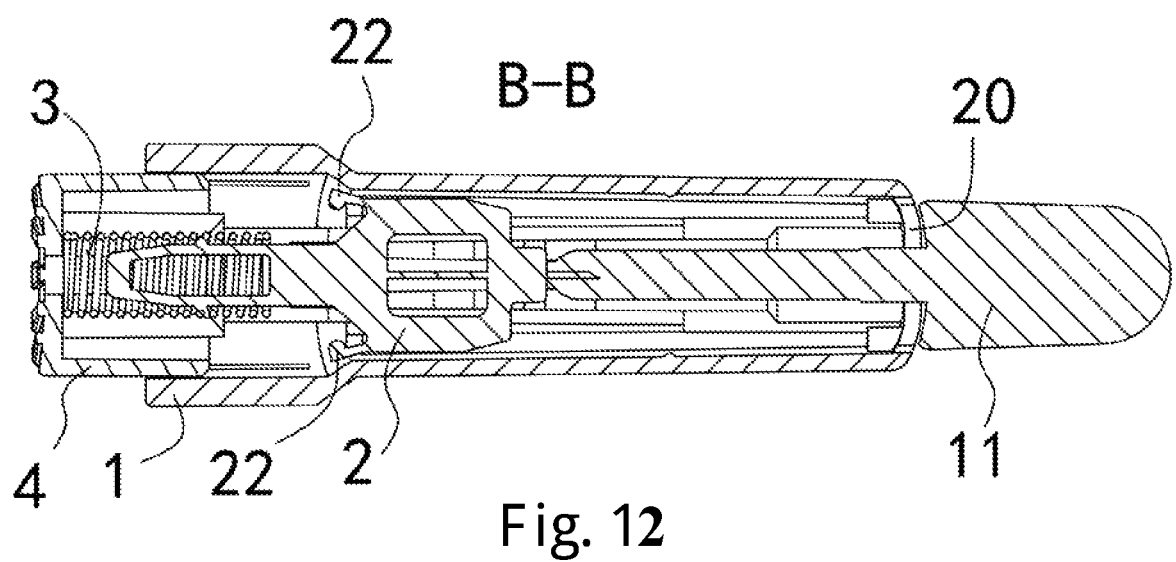
FIG. 12 is the B-B section view of an embodiment of present invention in the initial assembly state.
Figure 13:
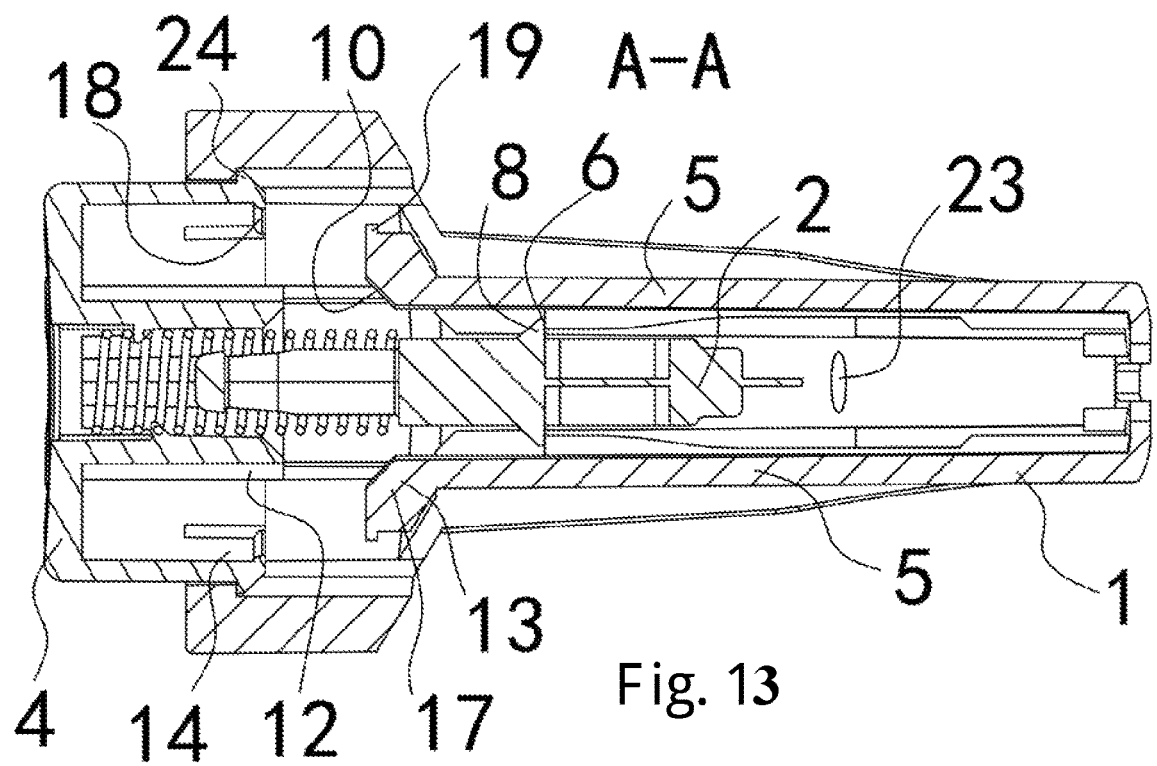
FIG. 13 is the A-A section view of an embodiment of present invention in the ejection ready state with the twist cap removed.
Figure 14:
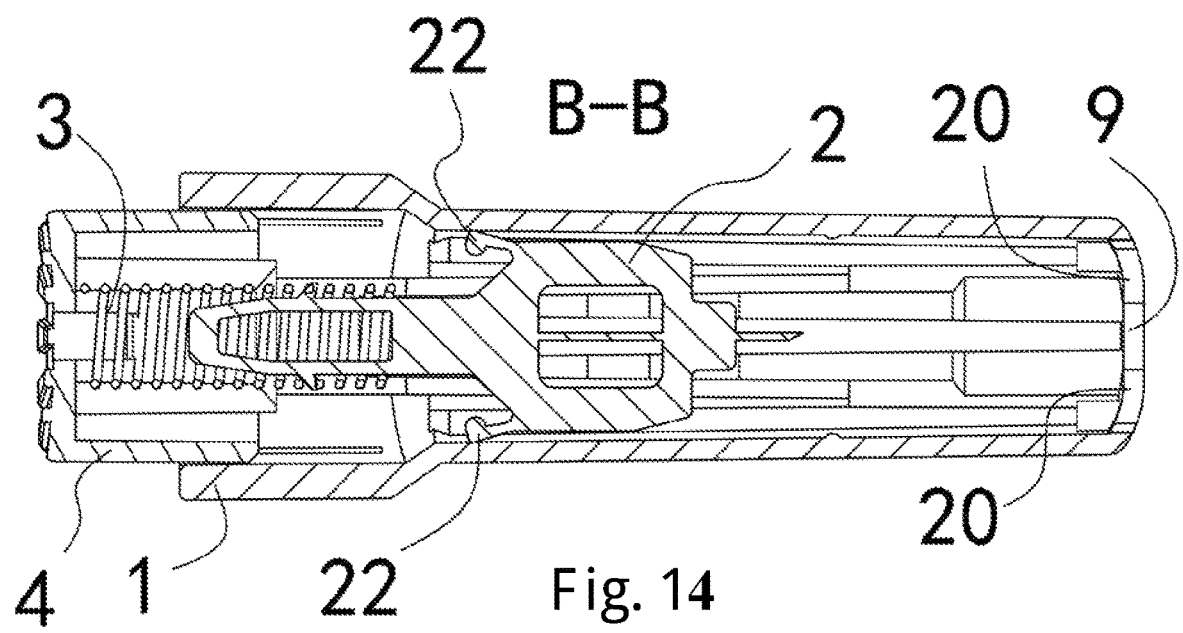
FIG. 14 is the B-B section view of an embodiment of present invention in the ejection ready state with the twist cap removed.

The shell 1 forms an ejecting cavity, and the ejecting cavity is provided with a needle outlet hole 9 at its front end (see FIG. 3 and FIG. 4), and the needle outlet hole 9 is provided with a notch 20 (see FIG. 4, FIG. 12 and FIG. 14). The lancet core 2 is located in the ejecting cavity, and the shell is provided with two elastic arms 5 extending inward (see FIG. 3, FIG. 4 and FIG. 11), and the elastic arm 5 is provided with a hook 6 for locking the lancet core 2 (see FIG. 11), and the lancet core 2 is provided with a clamping face 8 corresponding to the hook 6 (see FIG. 5, FIG. 6 and FIG. 11). In the ejection ready state, the front end of the spring 3 presses against the lancet core 2, and the clamping face 8 of the lancet core 2 presses against the hook 6 of the elastic arm 5, so that the lancet core 2 is positioned and locked in the ejecting cavity of the shell 1 (see FIG. 13).

The lancet core 2 and the twist cap 11 are an integrated component (see FIGS. 5 and 6), thereby forming a twist cap type tail pressing disposable safety lancet. The twist cap 11 is positioned in the front of the lancet core 2 and it's connected with the lancet core 2 to be an injection molding structure and the twist cap 11 is formed by the fixed connection of a twisting part 15 and a protection rod 16 and a tetractile neck 7 that can be twisted off is provided between the protection rod 16 and the lancet core 2. The lancet core 2 is provided with an elastic leg 22 on the side (see FIG. 6), and the shell 1 is provided with a protruding rib 23 on the inner wall corresponding to the elastic leg 22 (see FIG. 13 and FIG. 17). During the ejection process of the lancet core 2, the elastic leg 22 and the protruding rib 23 are friction-fitted to prevent secondary puncturing. A boss 21 is provided between the twisting part 15 of the twist cap 11 and the protection rod 16 (see FIG. 5 and FIG. 11), and the boss 21 is used to prevent mis-triggering in the initial assembly state (The working principle will be explained in detail when the working process is introduced later).

Figure 7:
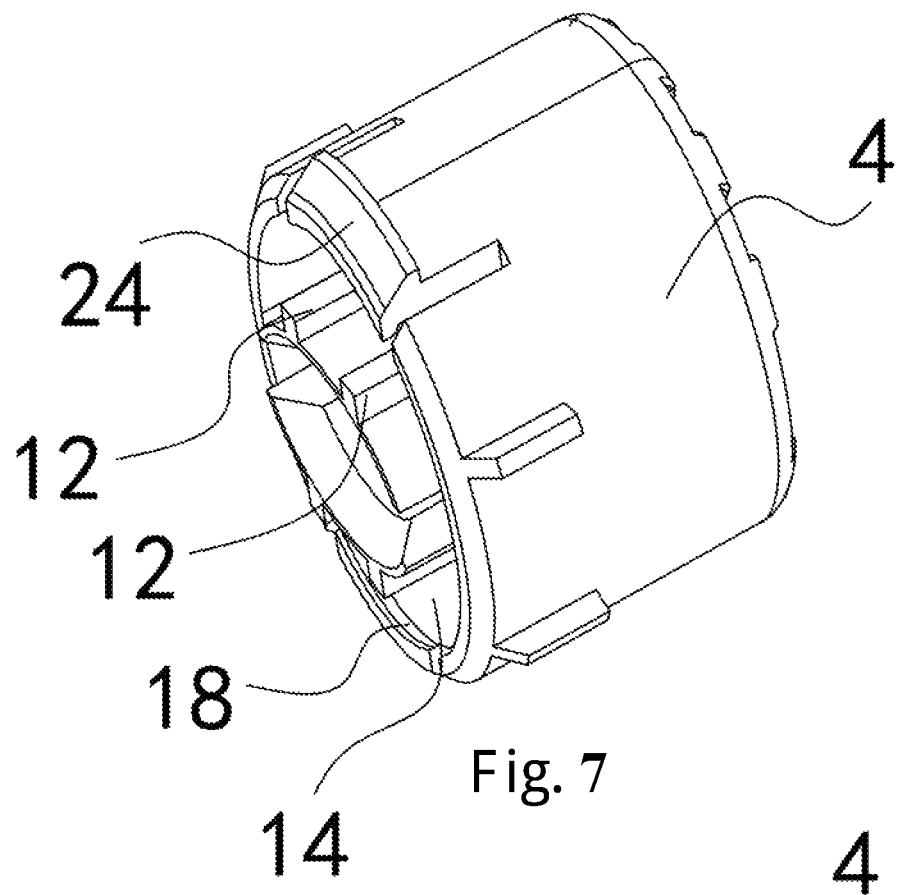
FIG. 7 is the first perspective view of the tail cover of an embodiment of present invention.
Figure 8:
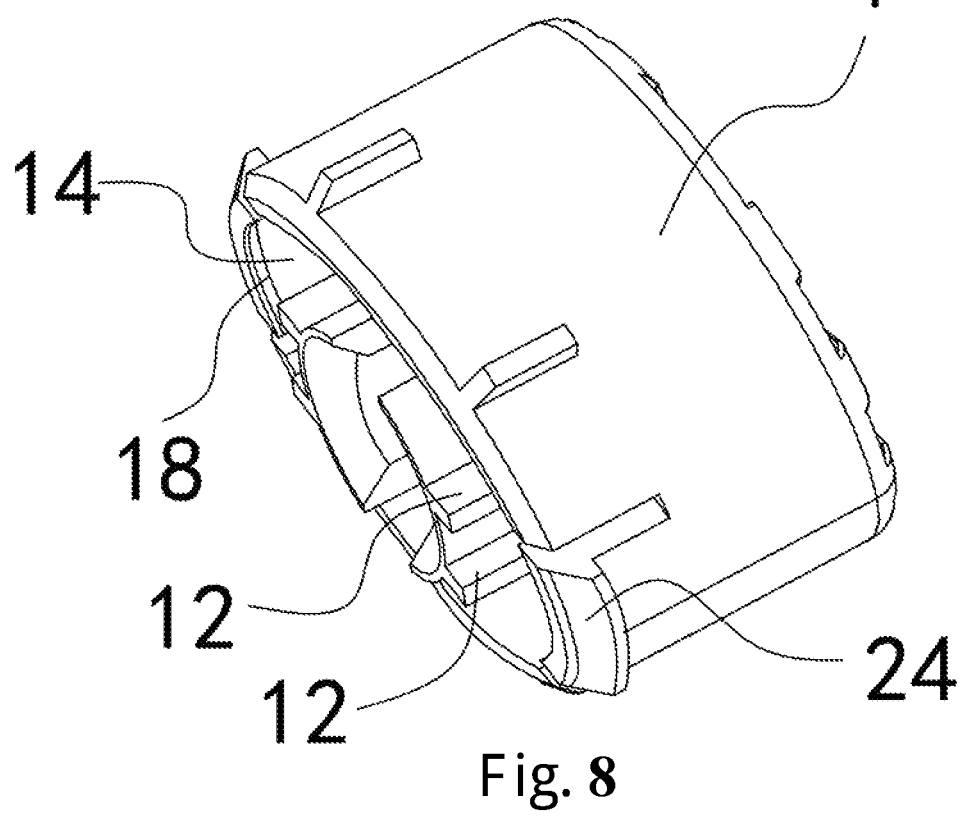
FIG. 8 is the second perspective view of the tail cover of an embodiment of present invention.
Figure 9:
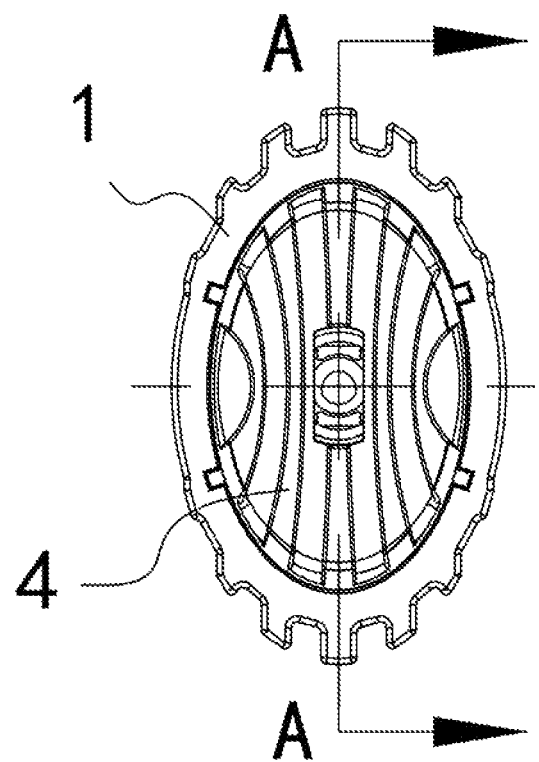
FIG. 9 is A-A section view of an embodiment of the invention taking the end face of the tail cover as a reference.
Figure 10:
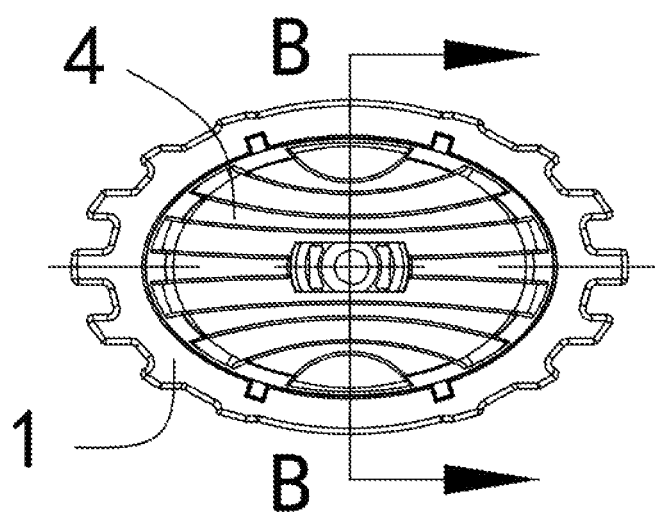
FIG. 10 is B-B section view of an embodiment of the invention taking the end face of the tail cover as a reference.

The tail cover 4 (see FIG. 7 and FIG. 8) is installed at the tail of the shell 1 (see FIG. 11 and FIG. 12), the tail cover 4 and the shell 1 are slidably connected in the axial direction of the safety lancet, and the tail cover 4 is provided with a limit relative to the rear end of the shell 1 in the sliding direction. It can be seen from FIG. 11 that there is an external hook 24 each at the top and bottom of tail cover 4 (also can be seen from FIG. 7 and FIG. 8), and the external hook 24 is located in the sliding channel of the shell 1, so that the tail cover 4 can be hooked on the shell 1 and slide in the axial direction of the safety lancet with respect to the shell 1. In the ejection ready state, the rear end of the spring 3 presses against the tail cover 4, and the external hook 24 is hooked on the rear end face of the sliding channel of the shell 1, forcing the tail cover 4 to the rear limit position in the sliding direction relative to the shell 1.

The tail cover 4 is provided with an active unlocking part 12 (see FIG. 7, FIG. 8 and FIG. 11), and the active unlocking part 12 is provided with an action end, and the elastic arm 5 is provided with a passive unlocking part 13 corresponding to the active unlocking part 12 (see FIG. 11), and the passive unlocking part 13 is provided with an action, and the action end of active unlocking part 12 is the corner of the lug (see FIG. 7, FIG. 8 and FIG. 11), and the action end of passive unlocking part 13 is the unlocking bevel 10 (see FIG. 11).

The tail cover 4 is provided with an active locking part 14 (see FIG. 7, FIG. 8 and FIG. 11), and the active locking part 14 is provided with an action end, and the elastic arm 5 is provided with a passive locking part 17 corresponding to the active locking part 14 (see FIG. 11), and the passive locking part 17 is provided with an action, and the action end of active locking part 14 is provided with a locking hook 18 (see FIG. 11), and the action end of passive locking part 17 is provided with a locking face 19 (see FIG. 11).

In the ejection ready state, taking the axial direction of the safety lancet as a reference, the axial projection distance between the action end (action point) of active unlocking part 12 and the action end (action point) of passive unlocking part 13 is less than the axial projection distance between the action end (action point) of active locking part 14 and the action end (action point) of passive locking part 17 (see FIG. 13). Taking the radial direction of the safety lancet as a reference, the distance between the action end (action point) of the active locking part 14 and the radial center of the safety lancet is greater than that between the action end (action point) of the passive locking part 17 and the radial center of the safety lancet (see FIG. 13).

The initial assembly state and the operation process of the embodiment of the present invention is as follows:

1. Initial Assembly State

As shown in FIG. 1 and FIG. 2, the lancet core 2 and the twist cap 11 are an integrated structure, and the lancet core 2 and the protective rod 16 on the twist cap 11 are located in the shell 1, and the twisting part 15 on the twist cap 11 is located outside the front end of the shell 1. The boss 21 provided between the twisting part 15 and the protection rod 16 abuts against the inner end face of the needle outlet hole 9 at the front end of the shell 1. The front end of the spring 3 presses against the back of the lancet core 2, the rear end of the spring 3 presses against the tail cover 4, and the external hook 24 of the tail cover 4 is hooked on the rear end face of the sliding channel of the shell 1, forcing the tail cover 4 to the rear limit position in the sliding direction relative to the shell 1. In this state, the hook 6 on the elastic arm 5 and the clamping face 8 on the lancet core 2 are in a non-locking state (the two are separated without contact and fitting, see FIG. 11). At this time, even if the tail cover 4 is pressed, the safety lancet can't be triggered as the boss 21 abuts against the inner end face of the needle outlet hole 9 at the front end of the shell 1, that is, when the twist cap 11 is not removed, pressing the tail cap 4 cannot trigger the lancet core 2 to eject. Therefore, in the initial assembly state, the function of the boss 21 is to prevent the mis-ejection of the safety lancet.

2. In the Ejection Ready State

Figure 15:
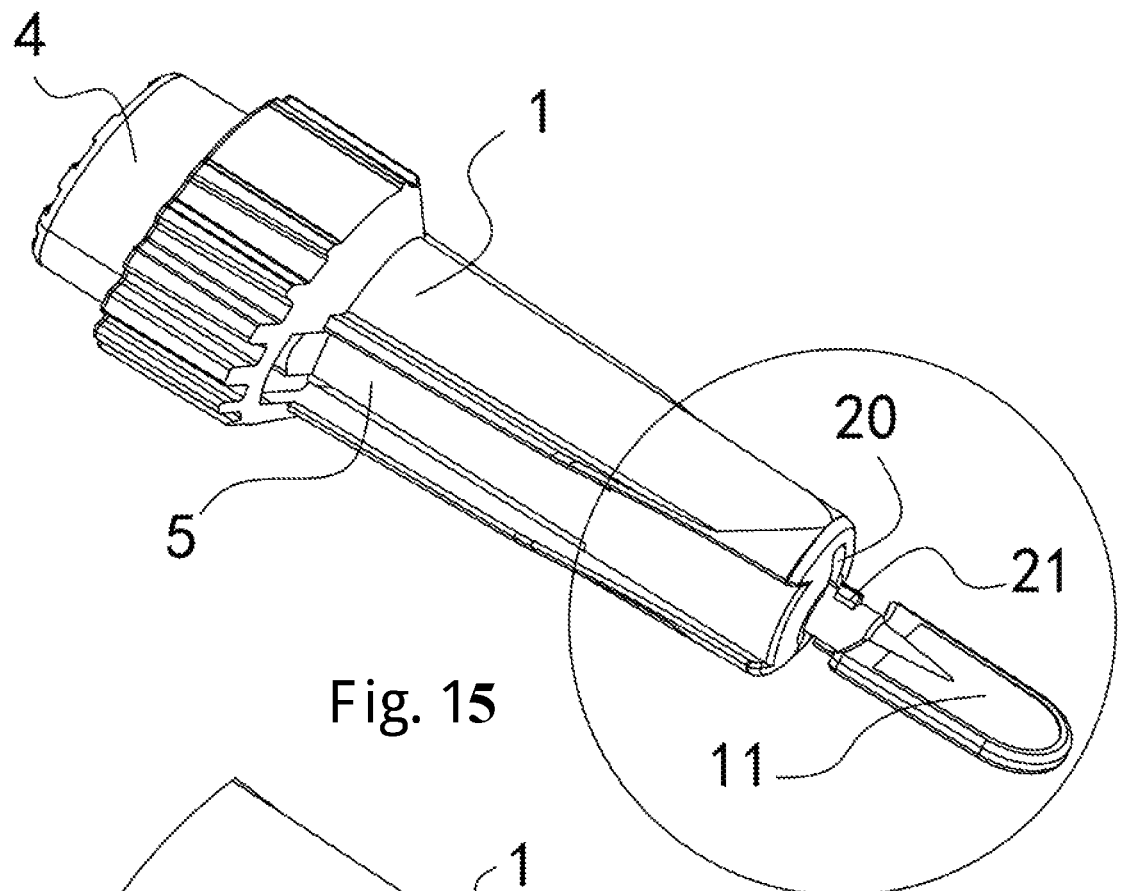
FIG. 15 is the perspective view of an embodiment of present invention in the ejection ready state with the twist cap removed.
Figure 16:
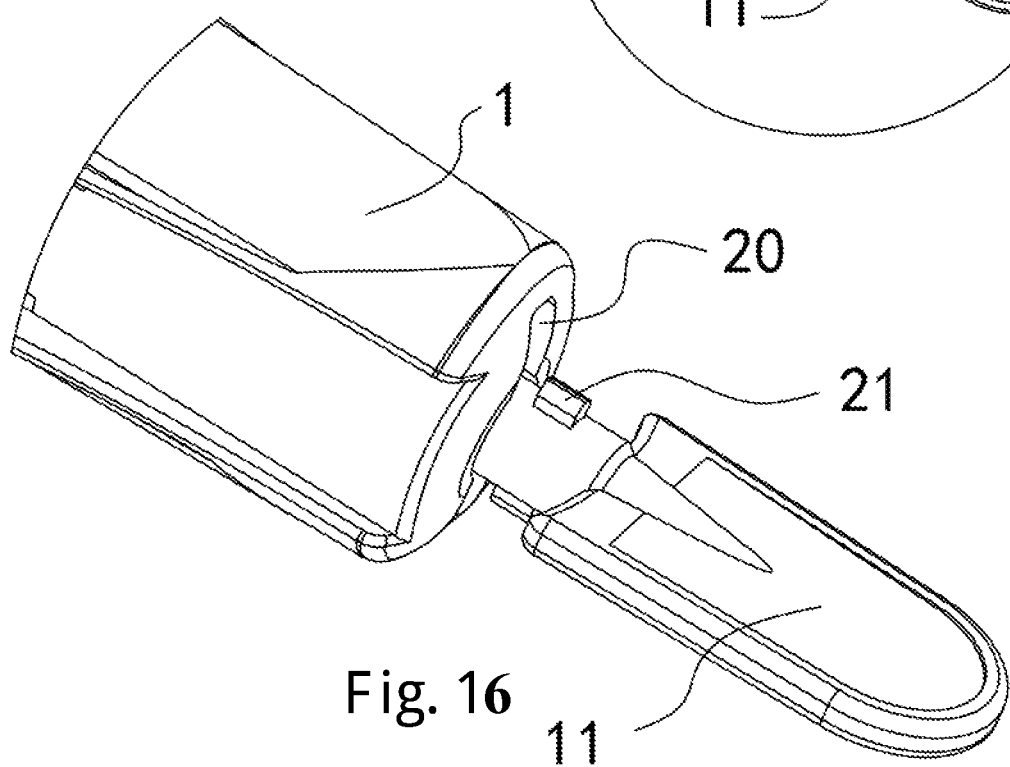
FIG. 16 is a local enlarged view of FIG. 15.

As shown in FIG. 13 and FIG. 14, before using the safety lancet, twist off the twist cap 11, that is, turn the twist cap 11 by 90°, forcing the twist cap 11 and the lancet core 2 to break at the tetractile neck 7 (see FIG. 5) and align the boss with the notch 20 on the needle outlet hole 9 and then pull out the twist cap 11 (see FIG. 15 and FIG. 16). At this time, the lancet core 2 moves forward by 2 mm under the force of the spring 3, and the clamping face 8 on the lancet core 2 is blocked by the hook 6 on the elastic arm 5, so that the lancet core 2 is locked by the hook 6 on the elastic arm 5 to enter the ejection ready state.

3. State of Starting to Press the Tail Cover

Figure 17:
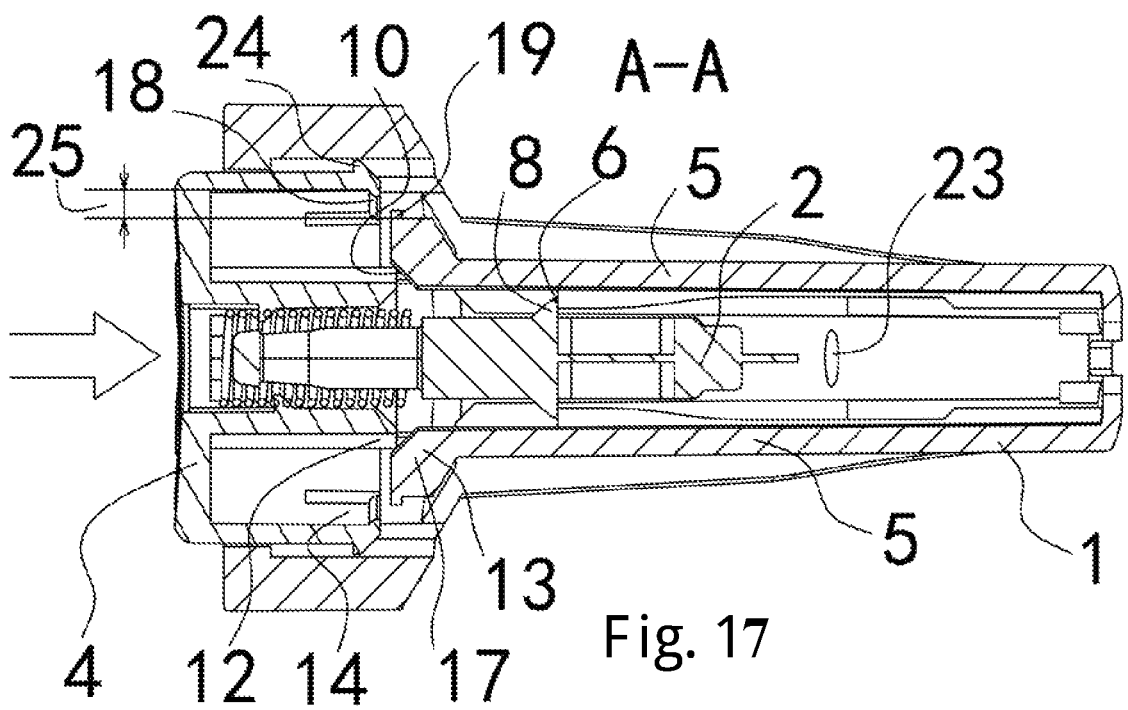
FIG. 17 is the A-A section view of an embodiment of present invention in the state of starting to press the tail cover.
Figure 18:
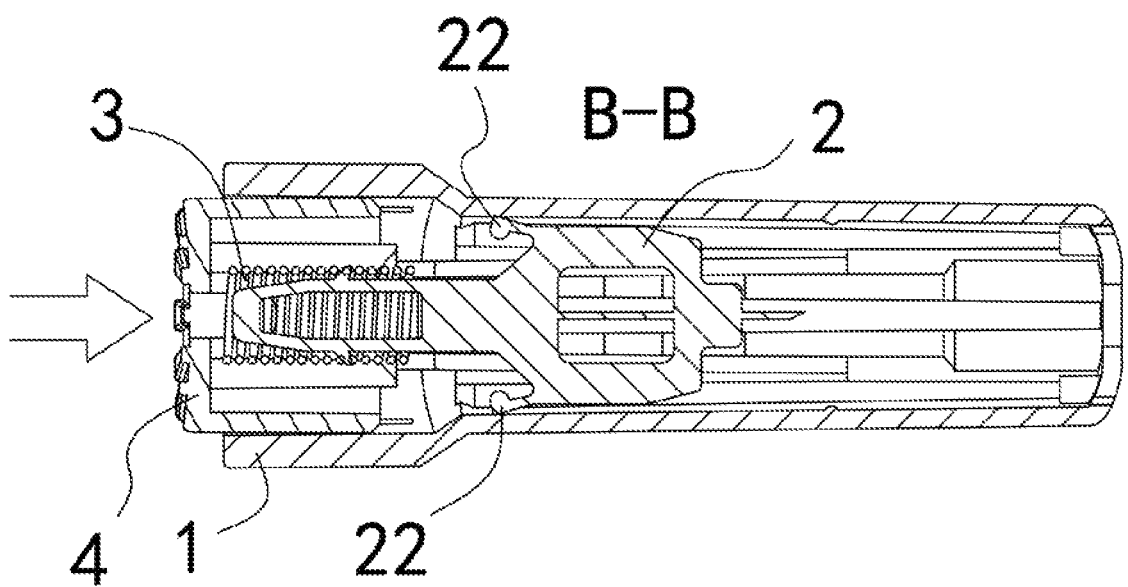
FIG. 18 is the B-B section view of an embodiment of present invention in the state of starting to press the tail cover.

As shown in FIG. 17 and FIG. 18, align the needle outlet hole 9 on the head of the safety lancet with the blood sampling site and start to press the tail cover 4 (see the arrow in FIG. 17 and FIG. 18), and the tail cover 4 moves forward, and the action end (corner of the lug) of the active unlocking part 12 on the tail cover 4 contacts the action end (unlocking bevel 10) of the passive unlocking part 13 on the elastic arm 5 (see FIG. 17).

4. Pre-Ejection State

Figure 19:
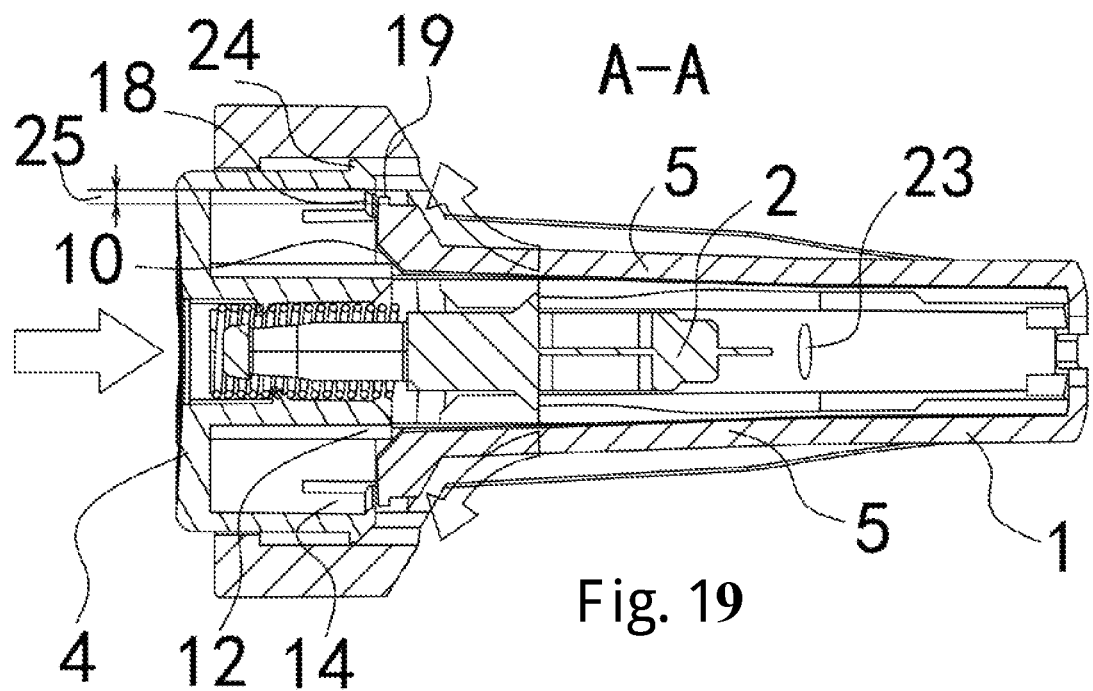
FIG. 19 is the A-A section view of an embodiment of present invention before ejection.
Figure 20:
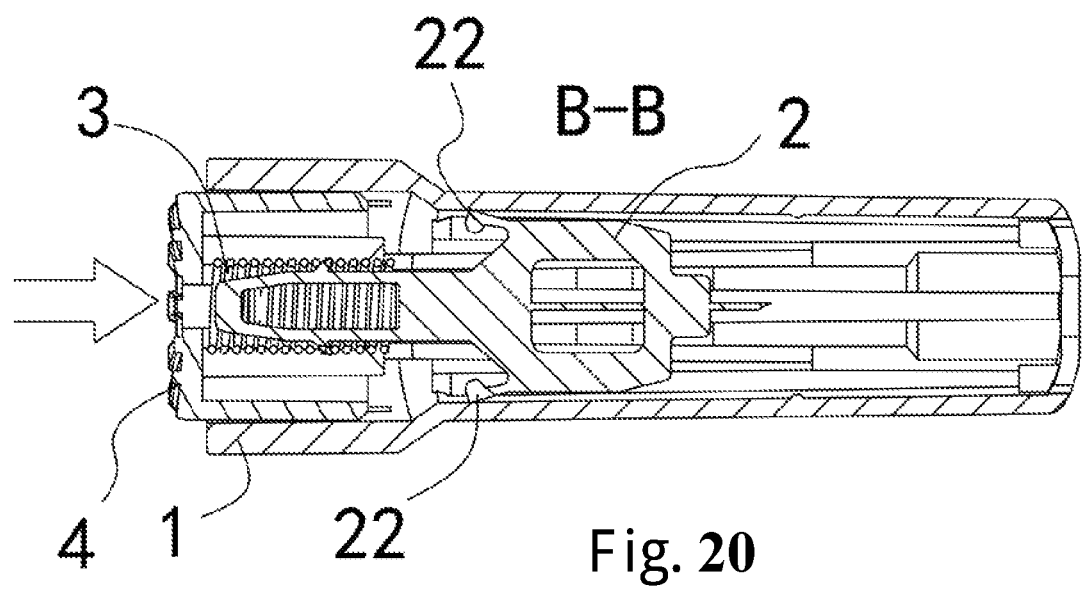
FIG. 20 is the B-B section view of an embodiment of present invention before ejection.

As shown in FIG. 19 and FIG. 20, continue to press the tail cover 4, the action end of the active unlocking part 12 on the tail cover 4 (the corner of the lug) meets the action end of the passive unlocking part 13 on the elastic arm 5 (the unlocking bevel 10) to force the end of the elastic arm 5 to laterally expand under the action of the unlocking bevel 10 (see the lateral expansion arrow in FIG. 19) and at the same time, the gap 25 is gradually changed from being larger in FIG. 17 to smaller in FIG. 19. The gap 25 is the radial gap between the action end (action point) of the active locking portion 14 and the action end (action point) of the passive locking portion 17 in the radial direction of the safety lancet.

5. In the Ejection State

Figure 21:
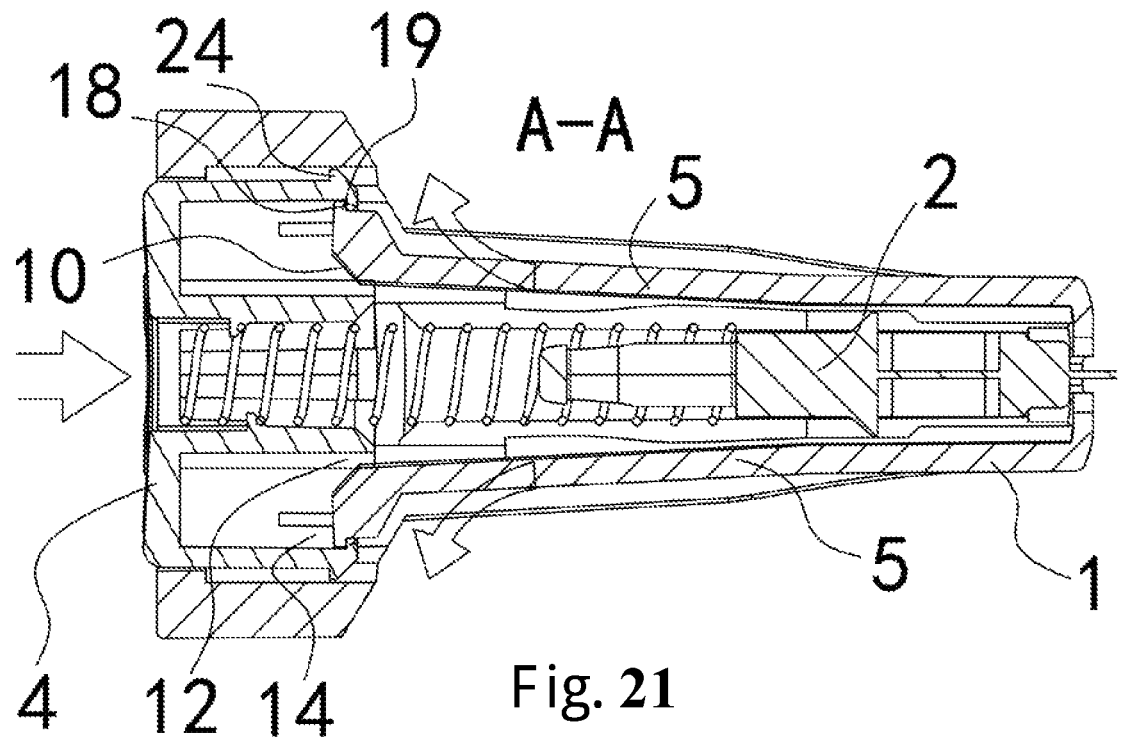
FIG. 21 is the A-A section view of an embodiment of present invention in the ejection state.
Figure 22:
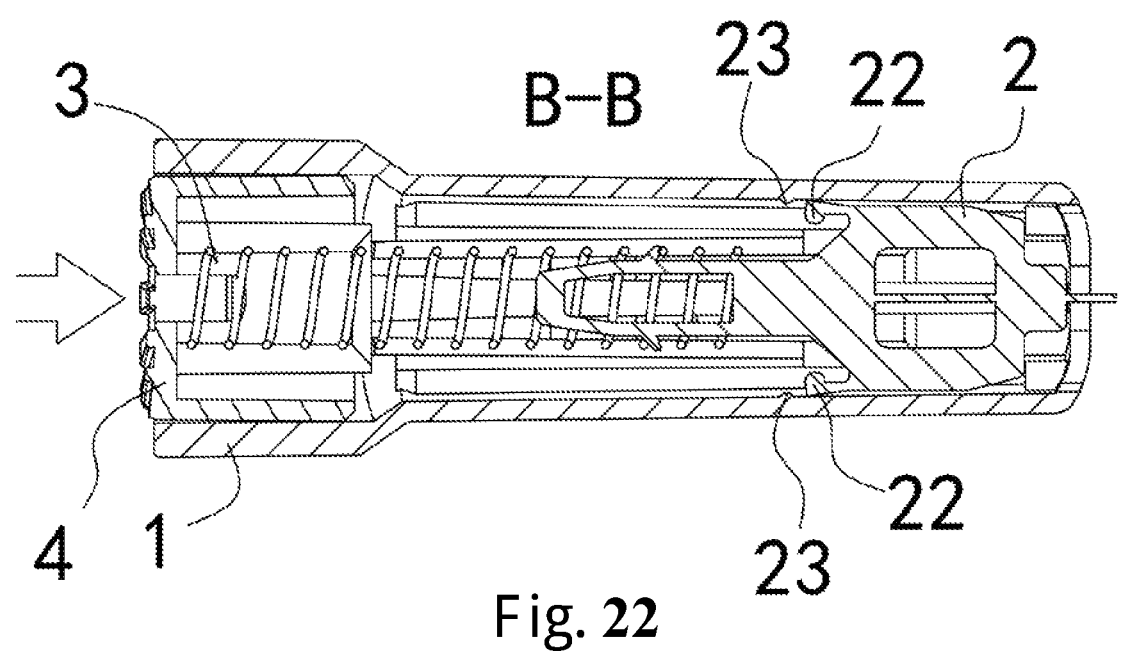
FIG. 22 is the B-B section view of an embodiment of present invention in the ejection state.
Figure 27:
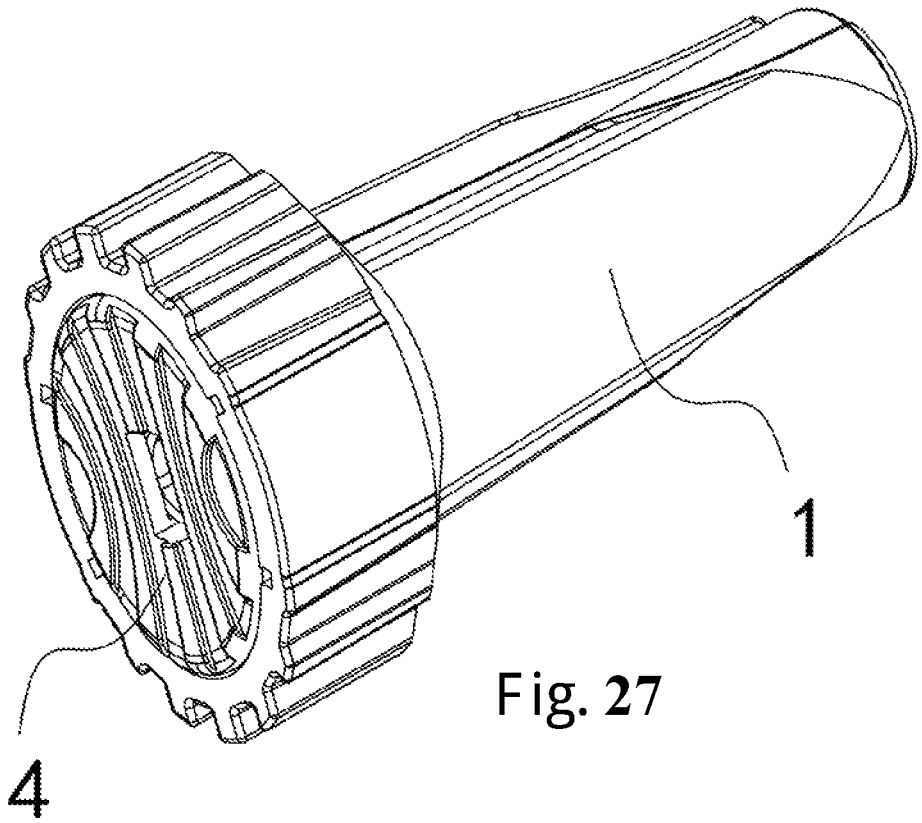
FIG. 27 is the perspective view of an embodiment of present invention after ejection with the tail cover in the retracted state.

As shown in FIG. 21 and FIG. 21, continue to press the tail cover 4, when the hook 6 on the elastic arm 5 is out of the locking critical point, the lancet core 2 is ejected to puncture under the action of the spring 3 to complete the blood sampling (see FIG. 21). After the ejection and puncturing, since the end of the elastic arm 5 is in a laterally expanded state, the action end of the passive locking part 17 is close to the action end of the active locking part 14 (the gap 25 is close to zero), and at this time, the tail cover 4 continues to move forward, the action end of the active locking part 14 on the tail cover 4 and the action end of the passive locking part 17 on the elastic arm 5 force the tail cover 4 and the elastic arm 5 into the locking hook state through the fitting of the locking hook 18 and locking face 19 and the tail cover 4 cannot rebound (see FIG. 21). In the locking hook state, the tail cover 4 is in a retracted state at the tail of the safety lancet (see FIG. 27).

6. Post-Ejection State

Figure 23:
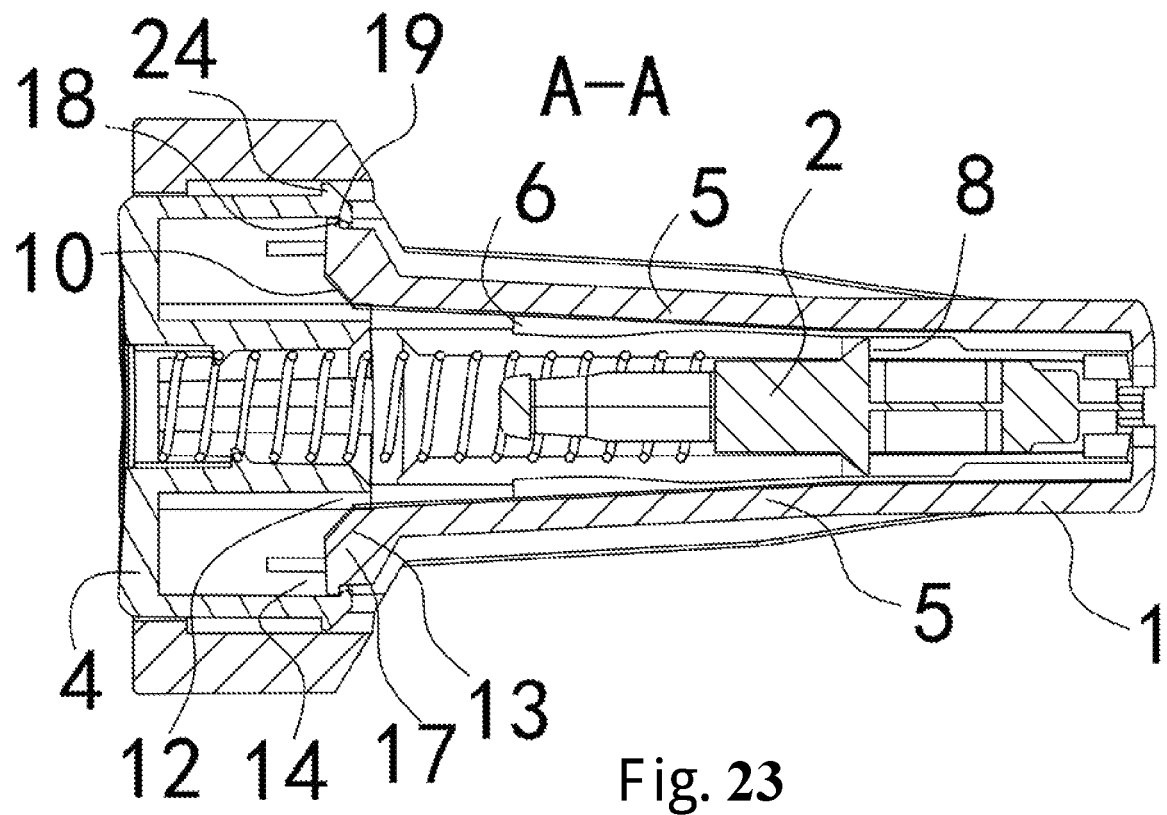
FIG. 23 is the A-A section view of an embodiment of present invention after ejection.
Figure 24:
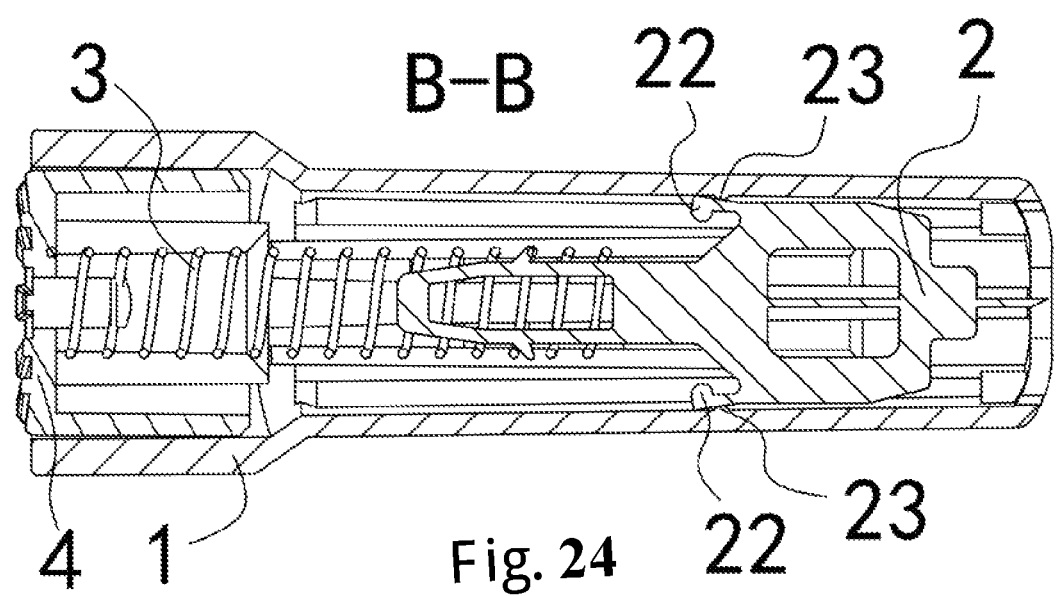
FIG. 24 is the B-B section view of an embodiment of present invention after ejection.

As shown in FIG. 23 and FIG. 24, when the lancet core 2 is ejected, the elastic legs 22 of the lancet core 2 smoothly passes the protruding ribs 23 on the inner wall of the shell 1. After the blood sampling is completed, the ribs 23 on the inner wall of the shell 1 will increase the friction with the elastic legs 22 of the lancet core 2, so that the elastic legs 22 on the lancet core 2 cannot pass the ribs 23 on the inner wall of the shell 1 so as to achieve the purpose of preventing secondary puncturing (see FIG. 24).

7. State after Use

Figure 25:
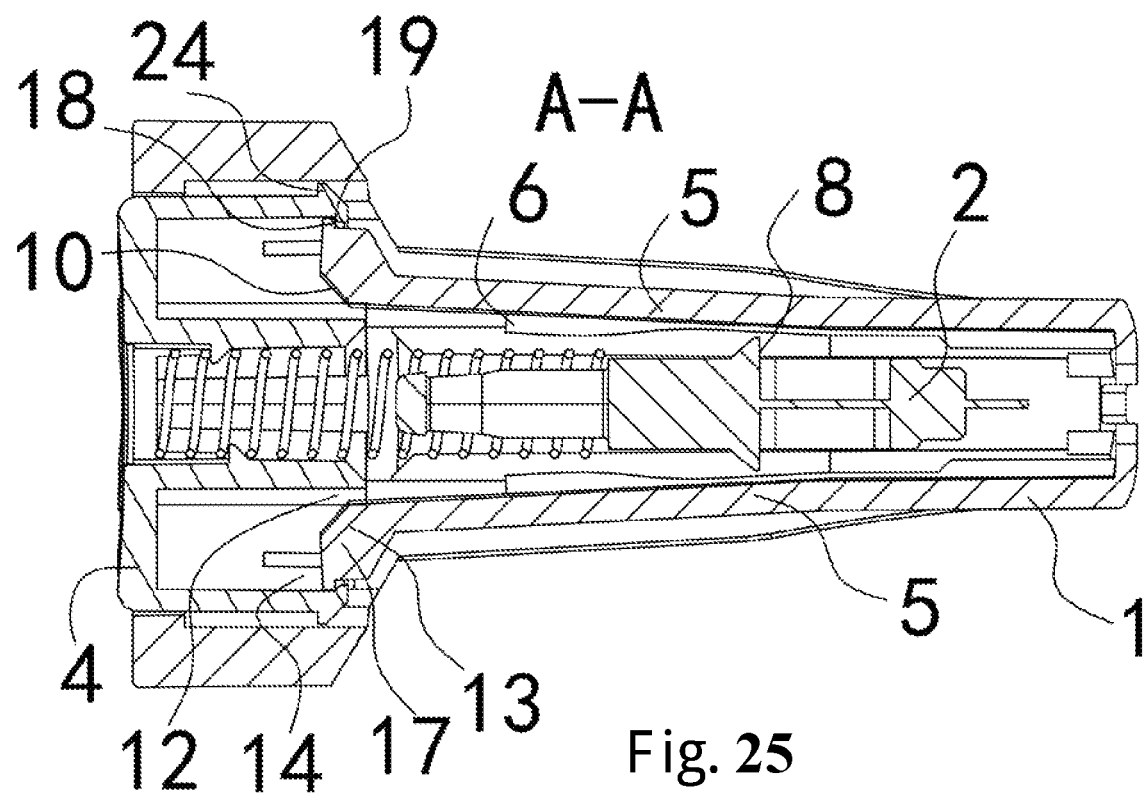
FIG. 25 is the A-A section view of an embodiment of the present invention after use.
Figure 26:
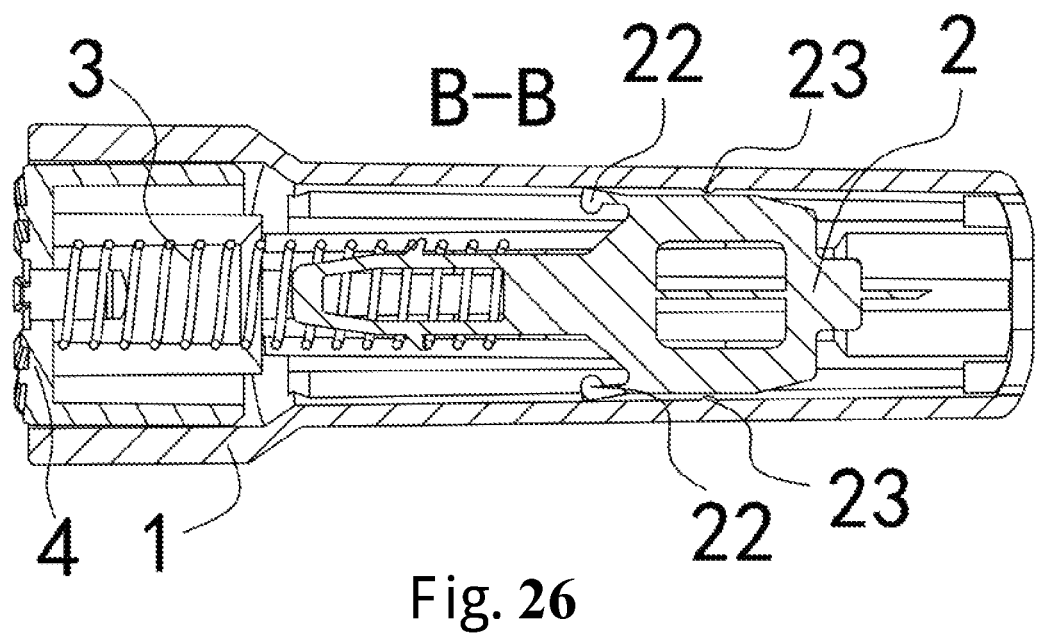
FIG. 26 is the B-B section view of an embodiment of the present invention after use.

As shown in FIG. 25 and FIG. 26, the tail cover 4, the spring 3 and the lancet core 2 all enter a stable state after use.

Figure 28:
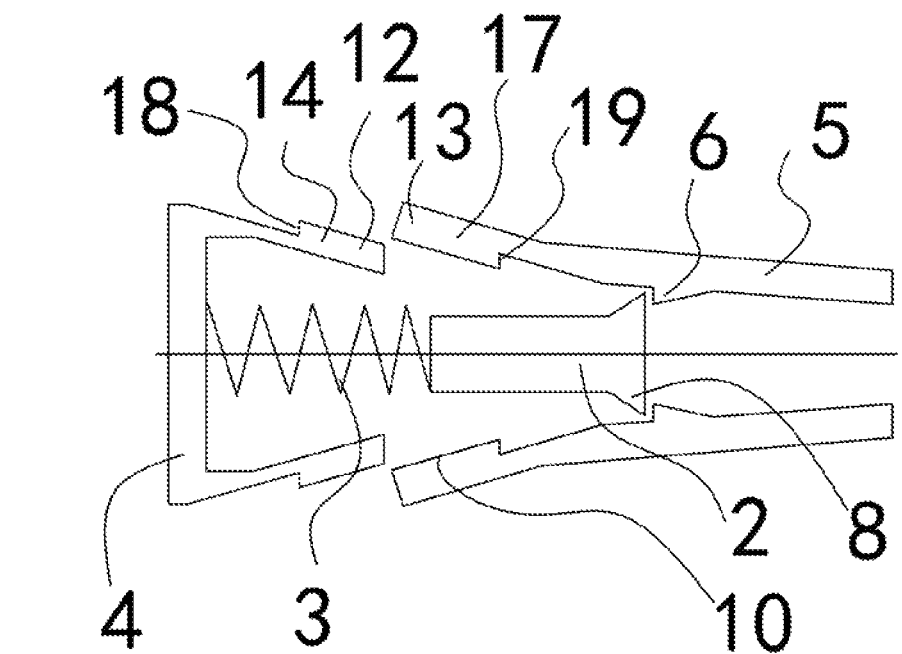
FIG. 28 is the schematic view of another variation of the embodiment of the present invention.

The following the description about the other embodiments and structural variations of the present invention:

1. In the above embodiment, the active unlocking part 12 and the active locking part 14 are two physical parts on the tail cover 4 (see FIG. 11), while the passive unlocking part 13 and the passive locking part 17 share a physical part on the elastic arm 5 (see FIG. 11). However, the present invention is not limited to this, and can also have the following variations:

(1) The active unlocking part 12 and the active locking part 14 share one physical part on the tail cover 4, while the passive unlocking part 13 and the passive locking part 17 share a physical part on the elastic arm 5 (see FIG. 28).

(2) The active unlocking part 12 and the active locking part 14 are two physical parts on the tail cover 4 while the passive unlocking part 13 and the passive locking part 17 are two physical parts on the elastic arm 5.

(3) The active unlocking part 12 and the active locking part 14 share one physical part on the tail cover 4 while the passive unlocking part 13 and the passive locking part 17 are two physical parts on the elastic arm 5.

2. In the above embodiment, the shell 1 is provided with two elastic arms 5 extending inward (see FIG. 11). However, the present invention is not limited to this. In addition to the two elastic arms 5 in the above embodiment, the present invention can also have the following variations:

(1) The quantity of elastic arm 5 provided on the shell 1 is one, and the elastic arm 5 and the inner wall of the shell 1 form an elastic clamp for locking the lancet core 2.

(2) The quantity of elastic arm 5 provided on the shell 1 is three, and all the elastic arms 5 are evenly distributed in the circumferential direction of the cross section of the shell 1 and form an elastic clamp for locking the lancet core 2.

(3) The quantity of elastic arm 5 provided on the shell 1 is four, and all the elastic arms 5 are evenly distributed in the circumferential direction of the cross section of the shell 1 and form an elastic clamp for locking the lancet core 2.

(4) The quantity of elastic arm 5 provided on the shell 1 is five, and all the elastic arms 5 are evenly distributed in the circumferential direction of the cross section of the shell 1 and form an elastic clamp for locking the lancet core 2.

More elastic arms 5 could be available, which is the variation that could be easily understood by those skilled in the art.

3. In the above embodiment, the elastic arm 5 is provided with a hook 6 for locking the lancet core 2. In the present invention, the hook 6 can be changed into an end face, and the same technical effect can be obtained by using the end face to lock the lancet core 2, which could be understood and recognized by those skilled in the art.

4. [0012] In the above embodiment, in the ejection ready state and taking the axial direction of the safety lancet as a reference, the axial projection distance between the action end (action point) of active unlocking part 12 and the action end (action point) of passive unlocking part 13 is less than the axial projection distance between the action end (action point) of active locking part 14 and the action end (action point) of passive locking part 17 (see FIG. 13). In addition to that, in the present invention, the axial projection distance between the action end (action point) of active unlocking part 12 and the action end (action point) of passive unlocking part 13 is greater than the axial projection distance between the action end (action point) of active locking part 14 and the action end (action point) of passive locking part 17. Because when the axial projection distance between the action end (action point) of active unlocking part 12 and the action end (action point) of passive unlocking part 13 is equal to the axial projection distance between the action end (action point) of active locking part 14 and the action end (action point) of passive locking part 17, the unlocking of the lancet core 2 and the locking of the tail cover 4 are likely to interfere, resulting in instability of the operation of the safety lancet.

5. In the above embodiment, the action end of the passive unlocking part 13 is the unlocking bevel 10. However, the present invention is not limited to this. The unlocking bevel 10 can be provided on the action end of the active unlocking part 12, and can also be provided on the action end of the active unlocking part 12 and the action end of the passive unlocking part 13 at the same time.

6. In the above embodiment, the action end of the active locking part 14 is provided with a locking hook 18 (see FIG. 11), and the action end of the passive locking part 17 is provided with a locking face 19 (see FIG. 11). However, the present invention is not limited to this. It is also possible to provide a locking face 19 on the action end of the active locking part 14 and a locking hook 18 on the action end of the passive locking part 17.

7. In the above embodiment, the lancet core 2 is provided with a twist cap 11 in the front to from the twist cap type tail pressing disposal lancet structure, and it is apparent to those skilled in the art after reading this disclosure that the present invention is equally applicable to the cover cap type tail pressing disposal lancet structure, that is, the lancet core 2 is provided with a cover cap in the front to from the cover cap type tail pressing disposal lancet.

8. In the above embodiment, the head of the safety lancet is not designed with an adjusting head structure to change the puncturing depth. In order to solve the problem of adjusting the puncturing depth during blood sampling, the head of the shell could be provided with an adjusting head structure to change the puncturing depth. The adjusting head structure for changing the puncturing depth can be realized by using prior art, which is the variation that could be easily understood by those skilled in the art.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A tail pressing type disposable safety lancet consisting of a shell, a lancet core, a spring and a tail cover, wherein:
   the shell forms an ejecting cavity, the lancet core is located in the ejecting cavity, the shell is provided with at least one elastic arm extending inward, and the at least one elastic arm is provided with a hook or end face for locking the lancet core, and the lancet core is provided with a clamping face corresponding to the hook or end face; in an ejection ready state, a front end of the spring presses against the lancet core, and the clamping face of the lancet core presses against the hook or end face of the at least one elastic arm, so that the lancet core is positioned and locked in the ejecting cavity of the shell;
   the tail cover is installed at a tail of the shell, the tail cover and the shell are slidably connected in an axial direction of the safety lancet, and the tail cover is provided with a limit relative to a rear end of the shell in the axial direction; in the ejection ready state, a rear end of the spring presses against the tail cover, forcing the tail cover to be in a rear limit position relative to the shell in the axial direction;
   the tail cover is provided with an active unlocking part, and the active unlocking part is provided with an action end and the at least one elastic arm is provided with a passive unlocking part corresponding to the active unlocking part, and the passive unlocking part is provided with an action end, and at least one of the action end of the active unlocking part and the action end of the passive unlocking part is an unlocking bevel;
   the tail cover is provided with an active locking part, and the active locking part is provided with an action end and the at least one elastic arm is provided with a passive locking part corresponding to the active locking part, and the passive locking part is provided with an action end, and one of the action end of the active locking part and the action end of the passive locking part is provided with a locking hook and the other action end is provided with a locking face;
   in the ejection ready state, taking the axial direction of the safety lancet as a reference, an axial projection distance between the action end of the active unlocking part and the action end of the passive unlocking part is less than or greater than an axial projection distance between the action end of the active locking part and the action end of the passive locking part; taking a radial direction of the safety lancet as a reference, a distance between the action end of the active locking part and a radial center of the safety lancet is greater than that between the action end of the passive locking part and the radial center of the safety lancet;
   in a use state, when the tail cover is pushed, the tail cover moves forward relative to the shell, and the action end of the active unlocking part on the tail cover meets the action end of the passive unlocking part on the at least one elastic arm, and forces an end of the at least one elastic arm to open laterally under the action of the unlocking bevel, and when the hook or end face of the at least one elastic arm is out of a locking critical point, the lancet core is triggered under an action of the spring; after an ejection, the tail cover continues to move forward and the action end of the active locking part on the tail cover and the action end of the passive locking part on the at least one elastic arm fit with each other through the locking hook and the locking face, forcing the tail cover and the at least one elastic arm to enter a locking state and the tail cover is in a retracted state at a tail of the safety lancet.

2. The safety lancet of claim 1, wherein: the active unlocking part and the active locking part share one physical part on the tail cover while the passive unlocking part and the passive locking part share one physical part on the at least one elastic arm.

3. The safety lancet of claim 1, wherein: the active unlocking part and the active locking part are two physical parts on the tail cover while the passive unlocking part and the passive locking part are two physical parts on the at least one elastic arm.

4. The safety lancet of claim 1, wherein: a quantity of the at least one elastic arm provided on the shell is at least two elastic arms, and all of the at least two elastic arms are evenly distributed in the circumferential direction of the cross section of the shell and form an elastic clamp for locking the lancet core.

5. The safety lancet of claim 1, wherein: a quantity of an at least one elastic arm provided on the shell is one elastic arm, and the one elastic arm and the inner wall of the shell form an elastic clamp for locking the lancet core.

6. The safety lancet of claim 1, wherein: the lancet core is provided with a twist cap in a front to form a twist cap type tail pressing type disposable safety lancet.

7. The safety lancet of claim 6, wherein: the twist cap is positioned in the front of the lancet core and is connected with the lancet core and the twist cap is formed by a fixed connection of a twisting part and a protection rod and a tetractile neck that can be twisted off is provided between the protection rod and the lancet core.

8. The safety lancet of claim 1, wherein: the lancet core is provided with a cover cap in a front to form a cover cap type tail pressing type disposable safety lancet.

9. The safety lancet of claim 1, wherein: a shell head is provided with an adjusting head structure which can change a puncturing depth.

* * * * *